US010339645B2

(12) United States Patent
Shibayama et al.

(10) Patent No.: US 10,339,645 B2
(45) Date of Patent: Jul. 2, 2019

(54) DEFECT DETECTION DEVICE AND PRODUCTION SYSTEM

(71) Applicant: Nissan Motor Co., Ltd., Yokohama-shi, Kanagawa (JP)

(72) Inventors: Hirohisa Shibayama, Kanagawa (JP); Eiji Shiotani, Kanagawa (JP); Satoru Sakurai, Kanagawa (JP); Kiyokazu Sugiyama, Kanagawa (JP); Akira Shimizu, Kanagawa (JP); Daisuke Terada, Kanagawa (JP); Yoshitsugu Noshi, Kanagawa (JP); Yoshito Utsumi, Kanagawa (JP)

(73) Assignee: Nissan Motor Co., Ltd., Yokohama-shi, Kanagawa (JP)

( * ) Notice: Subject to any disclaimer, the term of this patent is extended or adjusted under 35 U.S.C. 154(b) by 42 days.

(21) Appl. No.: 15/720,077

(22) Filed: Sep. 29, 2017

(65) Prior Publication Data

US 2018/0025486 A1    Jan. 25, 2018

Related U.S. Application Data

(62) Division of application No. 15/324,250, filed as application No. PCT/JP2014/068193 on Jul. 8, 2014, now Pat. No. 9,805,457.

(51) Int. Cl.
*G06K 9/00*    (2006.01)
*G06T 7/00*    (2017.01)
(Continued)

(52) U.S. Cl.
CPC .............. *G06T 7/0004* (2013.01); *B05B 9/01* (2013.01); *B05B 13/06* (2013.01); *B23Q 17/24* (2013.01);
(Continued)

(58) Field of Classification Search
None
See application file for complete search history.

(56) References Cited

U.S. PATENT DOCUMENTS 5,196,716 A    3/1993  Moriya et al.
5,799,104 A *  8/1998  Nakamura ................ G03F 1/26
                                                 250/492.2
(Continued)

FOREIGN PATENT DOCUMENTS

JP    H04169807 A    6/1992
JP    H05322792 A    12/1993
(Continued)

*Primary Examiner* — Shervin K Nakhjavan
(74) *Attorney, Agent, or Firm* — Young Basile Hanlon & MacFarlane, P.C.

(57) ABSTRACT

Provided is a defect detection device capable of measuring the volume of surface defects. The defect detection device includes: an imaging device configured to image an image of an inspection object; a binarization processing unit configured to subject the image to first and second binarization processing by use of different first and second binarization thresholds, so as to calculate first and second sizes for an identical defect in the image; a ratio calculation unit configured to calculate a first ratio of the second size to the first size; and a depth determination unit configured to determine a depth of the defect depending on the first ratio.

6 Claims, 10 Drawing Sheets

(51) Int. Cl.
  *B24B 33/02* (2006.01)
  *B23Q 17/24* (2006.01)
  *G01B 11/30* (2006.01)
  *G01B 11/22* (2006.01)
  *G01N 21/88* (2006.01)
  *G06T 7/507* (2017.01)
  *B05B 9/01* (2006.01)
  *B05B 13/06* (2006.01)
  *G01N 21/954* (2006.01)
  *G06T 7/62* (2017.01)

(52) U.S. Cl.
  CPC .............. *B24B 33/02* (2013.01); *G01B 11/22* (2013.01); *G01B 11/30* (2013.01); *G01N 21/88* (2013.01); *G01N 21/954* (2013.01); *G06T 7/507* (2017.01); *G06T 7/62* (2017.01); *G01N 2021/9548* (2013.01); *G01N 2201/10* (2013.01); *G01N 2201/12* (2013.01); *G06T 2207/30108* (2013.01); *G06T 2207/30148* (2013.01)

(56) References Cited

U.S. PATENT DOCUMENTS

| | | | |
|---|---|---|---|
| 6,734,960 B1 | 5/2004 | Goto et al. | |
| 2002/0188917 A1* | 12/2002 | Yokoyama | G01N 21/9501 382/145 |
| 2004/0126909 A1* | 7/2004 | Obara | G06T 7/0004 438/14 |
| 2007/0052795 A1 | 3/2007 | Swanger et al. | |
| 2009/0087079 A1 | 4/2009 | Onoda | |
| 2012/0062728 A1 | 3/2012 | Oikawa et al. | |
| 2013/0155061 A1 | 6/2013 | Jahanshahi et al. | |
| 2013/0261989 A1 | 10/2013 | Plotnikov et al. | |

FOREIGN PATENT DOCUMENTS

| | | |
|---|---|---|
| JP | H10171981 A | 6/1998 |
| JP | H1123477 A | 1/1999 |
| JP | 2002324233 A | 11/2002 |
| JP | 2005069887 A | 3/2005 |
| JP | 2005121450 A | 5/2005 |
| JP | 2009085617 A | 4/2009 |
| JP | 2010276347 A | 12/2010 |
| JP | 2011232070 A | 11/2011 |
| JP | 2012237585 A | 12/2012 |

* cited by examiner

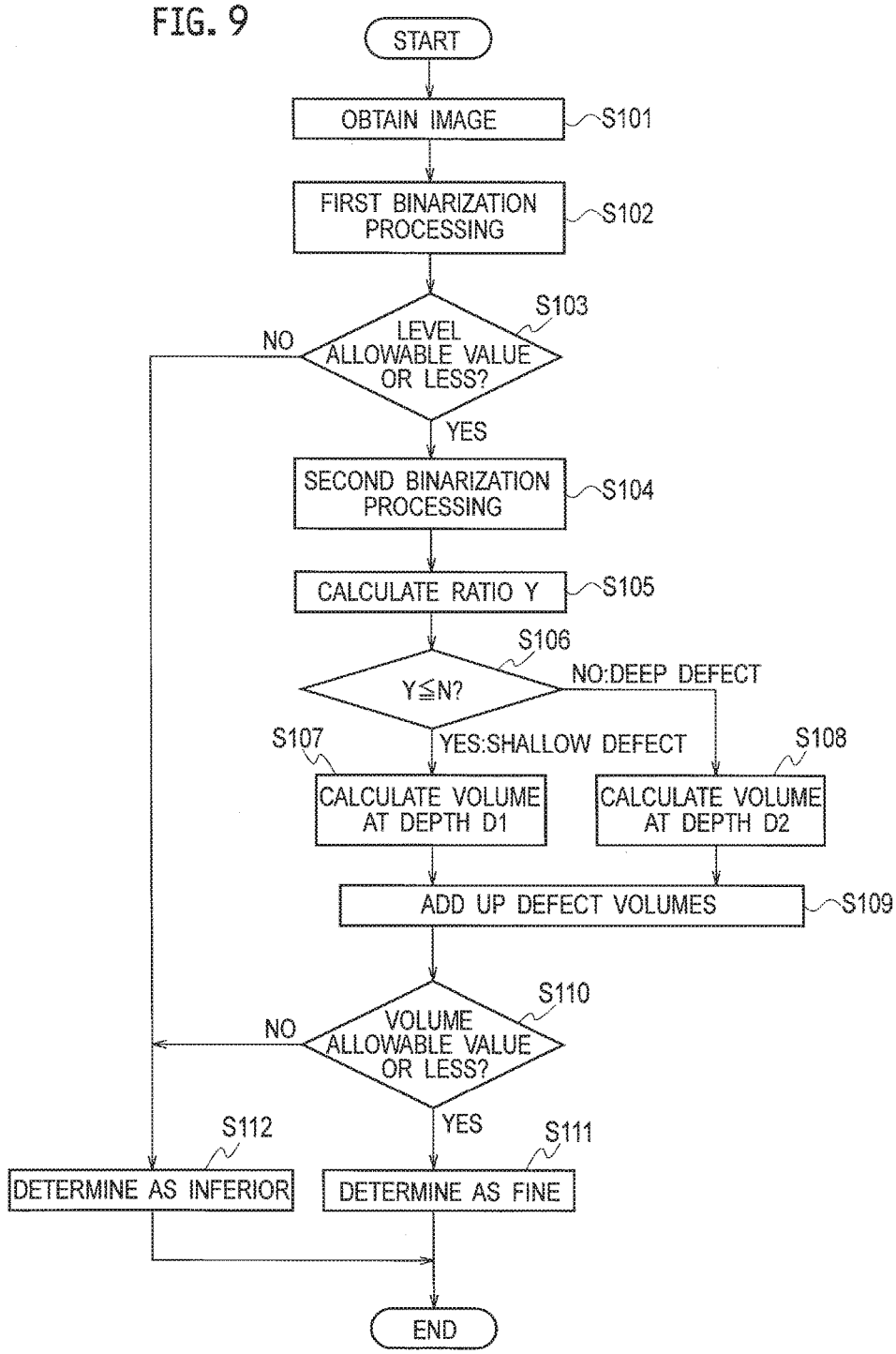

| DEFECT | FIRST DETERMINATION (RATIO Y1) | SECOND DETERMINATION (RATIO Y2) | OVERALL RATING |
|---|---|---|---|
| A | DEEP | DEEP | DEEP |
| B | DEEP | SHALLOW | INTERMEDIATE |
| C | SHALLOW | SHALLOW | SHALLOW |

| DEFECT | FIRST DETERMINATION (N1=0.5) | SECOND DETERMINATION (N2=0.7) | OVERALL RATING |
|---|---|---|---|
| A | DEEP | DEEP | DEEP |
| B | DEEP | SHALLOW | INTERMEDIATE |
| C | SHALLOW | SHALLOW | SHALLOW |

DEFECT DETECTION DEVICE AND PRODUCTION SYSTEM

CROSS-SECTION TO RELATED APPLICATIONS

This application is a divisional of U.S. patent application Ser. No. 15/324,250, which was filed on Jan. 5, 2017.

TECHNICAL FIELD

The present invention relates to a defect detection device and a production system.

BACKGROUND

Spraying technology (bore spraying) is known that sprays metal or ceramics to deposit coatings (sprayed coatings) on internal surfaces of cylinder bores of cylinder blocks installed in vehicles, and then implements honing processing thereon to form smooth sliding surfaces.

Since a sprayed coating is provided such that liquid droplets are applied to a surface in layers, the sprayed coating typically creates a porous structure including a plurality of pores and minute defects derived from iron oxide, for example. The porous structure may lead to minute surface defects because part of a surface layer of the sprayed coating comes off when after treatment such as honing is performed after spraying. In addition, the presence of casting cavities on the internal surface of the cylinder bore also leads to surface defects because a sprayed coating is not appropriately applied to the surface. While such surface defects serve as an oil collector and contribute to an improvement of lubrication of a piston linkage, the consumption of oil increases when the volume of defects is excessively large. It is therefore preferable to detect the surface defects on the internal surface of the cylinder bore and regulate the upper limit of the volume of the surface defects.

A typical method of detecting surface detects on an internal surface of a cylinder bore is to image the internal surface of the cylinder bore with, for example, a CCD camera to obtain a two-dimensional image, and detect the number and size of the surface defects from the two-dimensional image (for example, see Japanese Patent Application Publication No. H11-023477).

Japanese Patent Application Publication No. H11-023477 detects the number and size of the surface defects from the two-dimensional image, while the information about the depth of the defects is not obtained. Thus, a difficulty lies in measuring the volume of the surface defects on the internal surface of the cylinder bore with high accuracy.

SUMMARY

The present invention has been made in view of the above-described conventional problems. An object of the present invention is to provide a defect detection device and a production system capable of measuring the volume of surface defects with high accuracy.

A defect detection device and a production system according to an aspect of the present invention are configured to: image an image of an inspection object; subject the image to first and second binarization processing by use of different first and second binarization thresholds, so as to calculate first and second sizes for an identical defect in the image; calculate a first ratio of the second size to the first size; and determine a depth of the defect depending on the first ratio.

BRIEF DESCRIPTION OF THE DRAWINGS

FIG. 9 is a flowchart showing an example of a surface defect detection method according to the embodiment of the present invention;

DETAILED DESCRIPTION OF THE EMBODIMENTS

Figure 1:
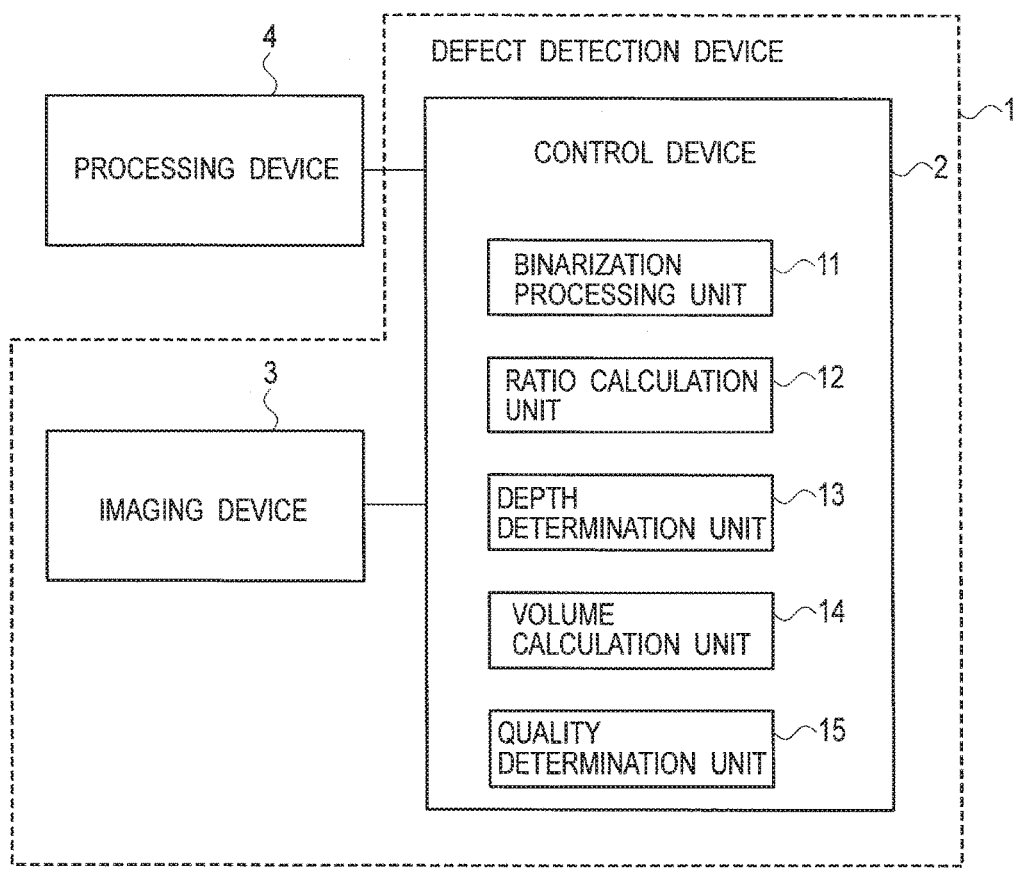
FIG. 1 is a block diagram showing an example of a configuration of a production system according to an embodiment of the present invention.

An embodiment will be described below with reference to the drawings. The same elements in the descriptions of the drawings are indicated by the same reference numerals, and explanations thereof are not repeated below.

[Production System and Defect Detection Device]

A production system according to an embodiment of the present invention includes a defect detection device 1 and a processing device 4, as shown in FIG. 1. The defect detection device 1 includes a control device 2 and an imaging device 3.

Figure 2:
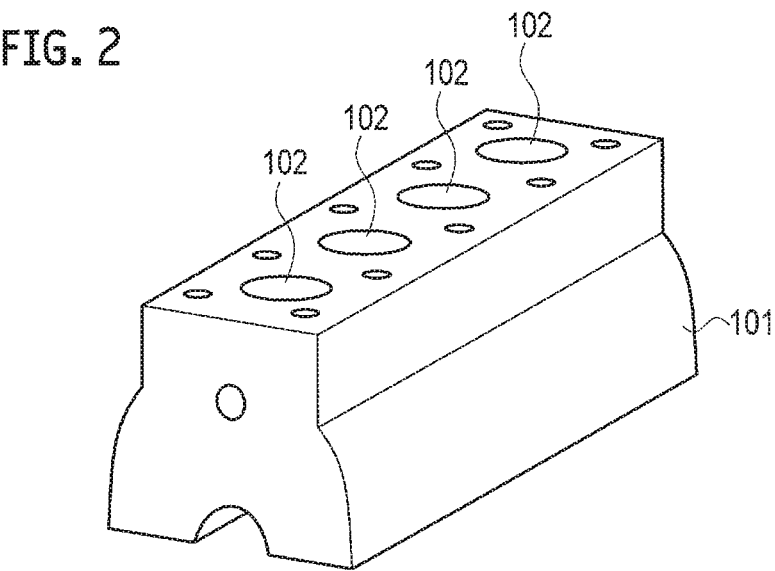
FIG. 2 is a schematic view showing an example of a cylinder block according to the embodiment of the present invention.

An inspection object by the defect detection device 1 according to the embodiment of the present invention is herein illustrated by a cylinder block of an engine for a vehicle. As shown in FIG. 2, a cylinder block 101 includes a plurality of cylinder bores 102 of cylindrical holes for housing pistons.

Figure 3:
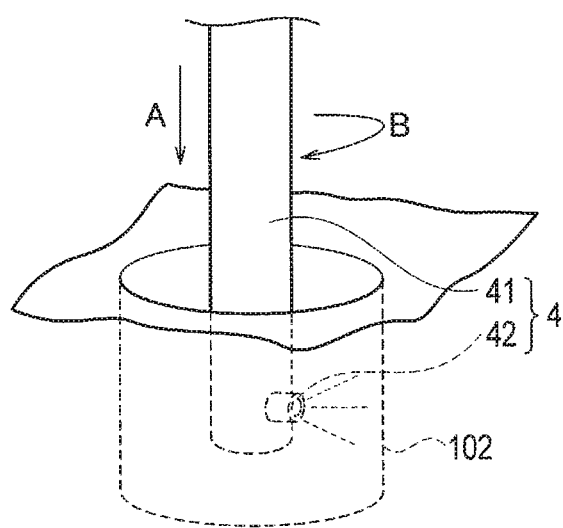
FIG. 3 is a schematic view showing an example of a configuration of a processing device according to the embodiment of the present invention.

The processing device 4 used may be a plasma spraying device. As shown in FIG. 3, the processing device (plasma spraying device) 4 includes a gun body 41, and a spray gun 42 protruding at the lower portion of the gun body 41. A bore spraying is obtained such that the gun body 41 moves in the direction of arrow A to enter a cylinder of the cylinder bore 102 of the cylinder block 101, and rotates in the circumferential direction B. At the same time, the spray gun 42 sprays a jet of metal or ceramics from the tip portion thereof onto the internal surface of the cylinder bore 102 of the cylinder block 101 so as to form a sprayed coating. The processing device 4 may be a device, such as a honing processing device, which may exert influence on surface defects of the sprayed coating, or may include several types of processing devices. Any device, as the processing device 4, that exerts influence on surface defects may be used as appropriate depending on the inspection object.

Figure 4:
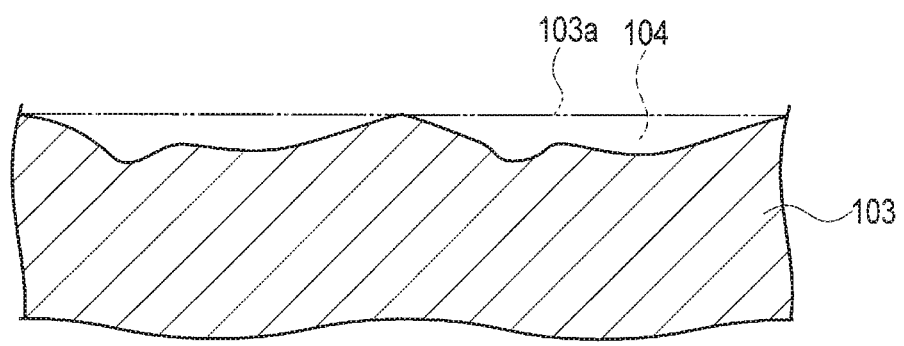
FIG. 4 is a sectional view showing an example of a sprayed coating including surface defects on an internal surface of a cylinder bore.

Since the sprayed coating is provided such that liquid droplets are applied to a surface in layers, the sprayed coating typically creates a porous structure including a plurality of pores and minute defects derived from iron oxide, for example. The porous structure may lead to minute surface defects (pits) 104 provided on a surface 103a because part of a surface layer of the sprayed coating 103 comes off when aftertreatment such as honing is performed after spraying, as schematically shown in FIG. 4. In addition, the presence of casting cavities on the internal surface of the cylinder bore 102 also leads to surface defects (blowholes) on the surface 103a because a sprayed coating is not appropriately applied to the surface of the blowholes. While such surface defects serve as an oil collector and contribute to an improvement of lubrication of a piston linkage, the consumption of oil increases when the volume of defects is excessively large. It is therefore preferable to detect the surface defects on the internal surface of the sprayed coating and regulate the upper limit of the sum of the volumes of the surface defects.

Examples of surface defects of the sprayed coating mainly include pits derived from aftertreatment, and blowholes derived from casting cavities, as described above. The diameter (maximum length) of blowholes is typically equivalent to or greater than the diameter (maximum length) of pits, and the depth of blowholes is typically five to ten times greater than the depth of pits. The surface defects of the sprayed coating 103 are not limited to pits and blowholes, but include recessed portions on the surface 103a.

Figure 5:
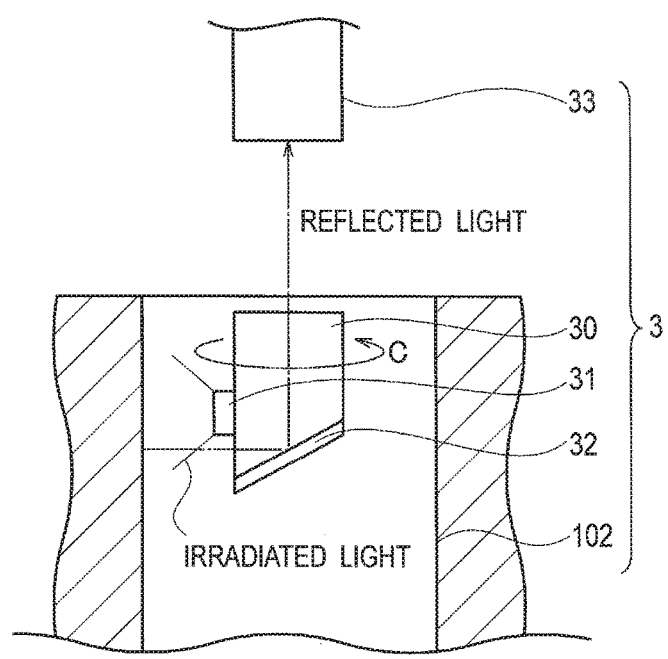
FIG. 5 is a schematic view showing an example of a configuration of an imaging device according to the embodiment of the present invention.

The imaging device 3, shown in FIG. 1, images a surface of the inspection object to obtain a two-dimensional image (a shaded image). As shown in FIG. 5, the imaging device 3 includes a drive unit 30, a light source 31 and a mirror 32 attached to the drive unit 30, and an imaging unit 33 fixed above the drive unit 30. The drive unit 30 enters the cylinder of the cylinder bore 102 as the inspection object, and rotates in the circumferential direction C. The light source 31 radiates the internal surface of the cylinder bore 102 with light. The mirror 32 reflects the light reflected from the inspection object to introduce the light into the imaging unit 33. The imaging unit 33 is, for example, a CCD camera, and images the surface of the inspection object by receiving the reflected light from the mirror 32, so as to obtain a two-dimensional image. Although the embodiment of the present invention exemplifies the imaging device 3 capable of imaging the internal surface of a cylindrical member such as the cylinder bore 102, the configuration of the imaging device 3 may change depending on the inspection object.

Figure 6:
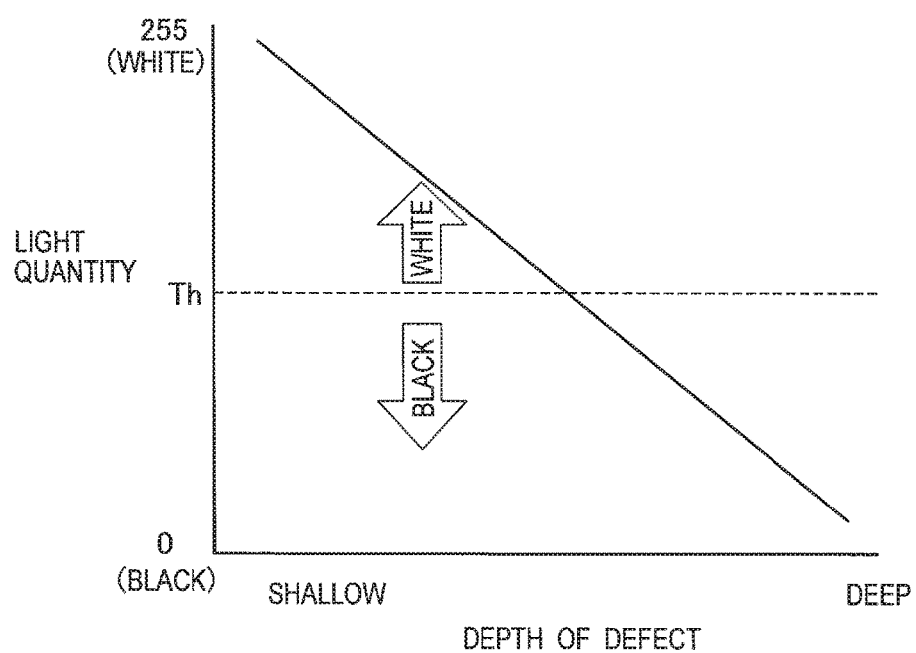
FIG. 6 is a graph showing an example of a relationship between a light quantity of pixels and a defect depth.

The two-dimensional image obtained by the imaging device 3 is a grayscale image with eight bits, for example, defined by the light quantity from black (0) to white (255) for each pixel. FIG. 6 shows an example of a relationship between the depth of surface defects of the sprayed coating and the light quantity of pixels. As shown in FIG. 6, the reflected light from the inspection object is relatively bright at a normal position where there is no surface defect on the inspection object, and the light quantity of pixels in the image increases. The reflected light from the inspection object is relatively dark at a position where surface defects are present on the inspection object, and the light quantity of pixels in the image decreases. In addition, as the surface defects are deeper, the light quantity of pixels in the image decreases.

The control device 2 shown in FIG. 1 includes a central processing unit (CPU), a RAM, a ROM, and a hard disk, for example. The control device 2 functionally includes a binarization processing unit 11, a ratio calculation unit 12, a depth determination unit 13, a volume calculation unit 14, and a quality determination unit 15.

The binarization processing unit 11 implements binarization processing on the two-dimensional image obtained by the imaging unit 33. As used herein, the term "binarization processing" represents the processing of converting each pixel having the light quantity of a grayscale two-dimensional image into either white or black by use of a binarization threshold. As shown in FIG. 6, when the light quantity of pixels is a predetermined binarization threshold Th or greater, the pixels are converted into white. When the light quantity of pixels is less than the predetermined binarization threshold Th, the pixels are converted into black. As the binarization threshold Th increases, the regions in black increase.

Figure 7:
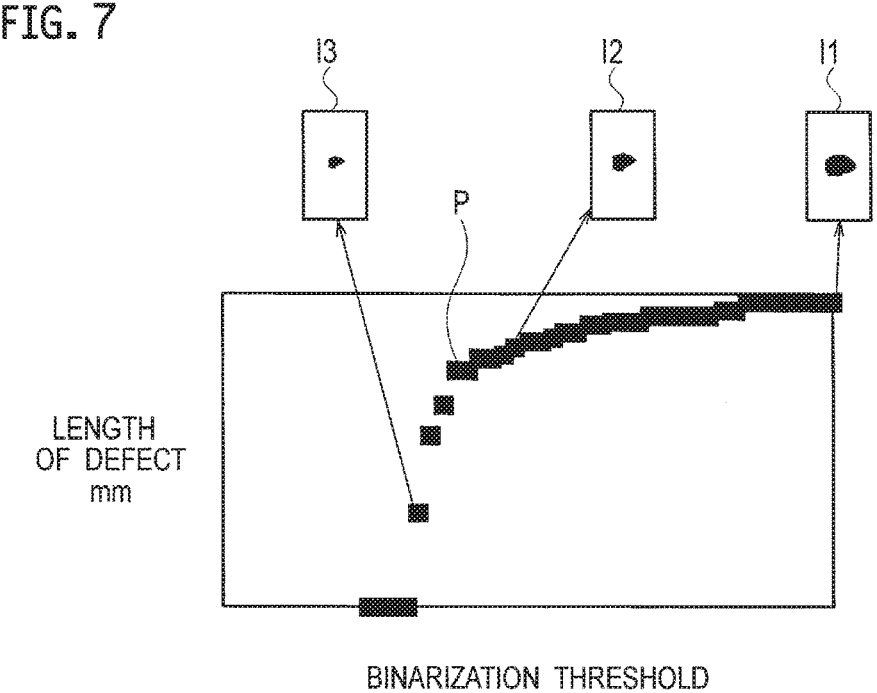
FIG. 7 is a graph showing an example of a relationship between a binarization threshold and a length of a defect detected.

FIG. 7 shows an example of variation in size (length) of a surface defect of the sprayed coating detected while changing a binarization threshold. As shown in FIG. 7, as the binarization threshold is larger, the size of a detected defect corresponding to an aggregation of black regions in the image is larger. FIG. 7 further schematically shows images 11 to 13 after subjected to the binarization processing by use of different binarization thresholds. As shown in FIG. 7, the size of the defect decreases in the order of the image 11, the image 12, and the image 13. In the example shown in FIG. 7, the relationship between the binarization threshold and the size of the surface defect nonlinearly varies, wherein the size of the surface defect gently decreases substantially in proportion to the decrease of the binarization threshold by the inflection point P, whereas the size of the surface defect starts decreasing sharply from the inflection point P.

The binarization processing unit 11 subjects the two-dimensional image obtained by the imaging unit 33 to (first and second) binarization processing twice by use of different first and second binarization thresholds Th1 and Th2. The first and second binarization thresholds Th1 and Th2 may be determined as appropriate depending on the product or the type of defects. The first binarization threshold Th is set to 100, for example. The second binarization threshold T2 is set to a smaller value than the first binarization threshold Th1, such as 50. The first and second binarization thresholds Th1 and Th2 are preliminarily stored in the memory of the control device 2, for example, and read out as necessary.

The binarization processing unit 11 detects defects each corresponding to an aggregation of black regions from each of the image after subjected to the first binarization processing and the image after subjected to the second binarization processing, and calculates the respective sizes for the same defect. The size of the defect includes at least one of the defect area or the defect length. The length of the defect calculated is a maximum length (greatest diameter), for example. The area of the defect calculated is an area of a circumcircle having the maximum length (greatest diameter), for example. The defect in the image subjected to the first binarization processing and the defect in the image subjected to the second binarization processing may be matched with each other by use of a positional coordinate. Since the first binarization threshold Th1 is larger than the second binarization threshold Th2, the size of the defect obtained by the first binarization processing by use of the first binarization threshold Th1 is greater than the size of the defect obtained by the second binarization processing by use of the second binarization threshold Th2.

Figure 8:
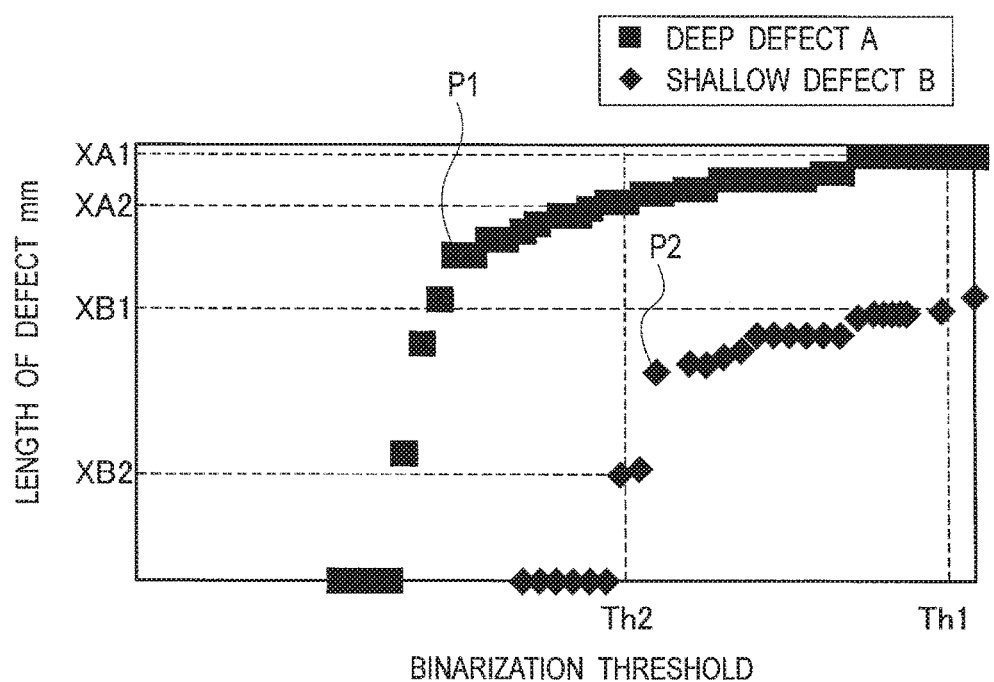
FIG. 8 is a graph showing an example of a relationship between a binarization threshold and a length of detected defects having different depths.

FIG. 8 exemplifies a case in which there are a relatively deep defect A (such as a blowhole) and a relatively shallow defect B (such as a pit). As shown in FIG. 8, the lengths of the detected defects A and B decrease as the respective binarization thresholds decrease, wherein a degree of variation of the lengths sharply increases from the respective particular inflection points P1 and P2. The binarization processing unit 11 subjects the defect A to the binarization processing by use of the first binarization threshold Th1 to detect a length XA1 of the defect A. The binarization processing unit 11 then subjects the defect A to the binarization processing by use of the second binarization threshold Th2 to detect a length XA2 of the defect A. The binarization processing unit 11 further subjects the defect B to the binarization processing by use of the first binarization threshold Th1 to detect a length XB1 of the defect B. The binarization processing unit 11 then subjects the defect B to the binarization processing by use of the second binarization threshold Th2 to detect a length XB2 of the defect B.

For example, with regard to the defect A, the ratio calculation unit 12 calculates a ratio Y of the size XA2 obtained by the second binarization processing to the size XA1 obtained by the first binarization processing (Y=XA2/XA1). When the defect detected by the first binarization processing is not detected by the second binarization processing, the size XA2 is 0, and the ratio Y calculated results in 0. Since the size XA1 obtained by the first binarization processing is greater than the size XA2 obtained by the second binarization processing, the ratio Y is in the range of 0 or larger and 1 or smaller.

The depth determination unit 13 determines (discriminates) the relative depth (deep or shallow) of the surface defect depending on the ratio Y. The depth determination unit 13 determines that the surface defect is shallow when the ratio Y is a threshold N or smaller, and determines that the surface defect is deep when the ratio Y is larger than the threshold N. The threshold N may be determined as appropriate in the range of larger than 0 and smaller than 1, depending on the product or the type of defects, and is set to 0.5, for example. The threshold N is preliminarily stored in the memory of the control device 2, for example, and read out as necessary. For example, the depth determination unit 13 determines that the defect A is deep when the ratio Y of the defect A is 0.8, which is larger than the threshold N set to 0.5. The depth determination unit 13 determines that the defect B is shallow when the ratio Y of the defect B is 0.4, which is smaller than the threshold N set to 0.5.

The volume calculation unit 14 sets the depth of the defect depending on the depth determined by the depth determination unit 13. For example, when the depth determination unit 13 determines that the defect is deep, the volume calculation unit 14 sets the depth of the defect to 100 μm. When the depth determination unit 13 determines that the defect is shallow, the volume calculation unit 14 sets the depth of the defect to 10 μm. The values of the depths of defects set depending on the depth determination results obtained by the depth determination unit 13 may be determined as appropriate depending on the product or the type of defects. The values set for the depths of defects are preliminarily stored in the memory of the control device 2, for example, and read out as necessary.

The volume calculation unit 14 then calculates the volume of the defect based on the set depth and the size of the defect. The size of the defect used may be the size of the defect obtained by the first binarization processing, the size of the defect obtained by the second binarization processing, or the average of the two sizes. For example, when the size (area) of the defect is 20 mm$^2$, and the depth of the defect is 100 μm, the volume calculated results in 2 mm$^3$. The volume calculation unit 14 also calculates the depths and volumes of all defects included in the image. The volume calculation unit 14 further adds up the volumes of the all defects to calculate the sum of the volumes of the defects.

The quality determination unit 15 determines whether the sum of the volumes of the defects calculated by the volume calculation unit 14 is an allowable value (threshold) or smaller. The quality determination unit 15 determines that the inspection object is fine when the sum of the volumes of the defects is the allowable value or smaller, and determines that the inspection object is inferior when the sum of the volumes of the defects is larger than the allowable value. The allowable value may be determined as appropriate depending on an allowable value of oil consumption, for example. The allowable value is preliminarily stored in the memory of the control device 2, for example, and read out as necessary.

The sum of the volumes of the defects calculated by the volume calculation unit 14 and the quality determination result determined by the quality determination unit 15 are fed back to the processing device 4. The processing device 4 arranges processing conditions so that the sum of the volumes of the defects is the allowable value or smaller, based on the sum of the volumes of the defects calculated by the volume calculation unit 14 and the allowable value thereof. Instead of the arrangement of the processing conditions by the processing device 4, or in addition to the arrangement of the processing conditions by the processing device 4, processing conditions for the processing process such as honing after plasma spray coating by the processing device 4 may also be arranged.

[Defect Detection Method]

Next, an example of a surface defect detection method according to the embodiment of the present invention is described below with reference to the flowchart shown in FIG. 9.

In step S101, the imaging device 3 images a surface of the inspection object to obtain a two-dimensional image. In step S102, the binarization processing unit 11 subjects the two-dimensional image obtained by the imaging device 3 to the first binarization processing by use of the first binarization threshold Th1. The binarization processing unit 11 then extracts defects from the image subjected to the first binarization processing, so as to calculate the size X1 of the defects.

In step S103, the quality determination unit 15 determines whether the size X1 of each defect after subjected to the first binarization processing is an allowable value (threshold) or smaller. The allowable value may be determined as appropriate depending on the product or the type of defects, and is set to 1.5 mm, for example. When defects greater than the allowable value are included, the process proceeds to step S112 to result in inferiority. When the size X1 of the all defects is determined as being the allowable value or smaller in step S103, the process proceeds to step S104.

In step S104, the binarization processing unit 11 subjects the two-dimensional image obtained by the imaging device 3 to the second binarization processing by use of the second binarization threshold Th2. The binarization processing unit 11 then extracts defects from the image subjected to the second binarization processing, so as to calculate the size X2 of the defects.

In step S105, the ration calculation unit 12 calculates, with regard to the same defect, the ratio Y of the size X2 of the defect obtained by the second binarization processing to the size X1 of the defect obtained by the first binarization processing (Y=X2/X1).

In step S106, the depth determination unit 13 determines whether the ratio Y calculated by the ratio calculation unit 12 is the threshold N or smaller, so as to determine the relative depth of the defect. When the ratio Y is the threshold N or smaller, the depth determination unit 13 determines that the defect is shallow (as a pit, for example), and the process proceeds to step S107. In step S107, the volume calculation unit 14 sets the depth D1 of the shallow defect. The volume calculation unit 14 further calculates the volume of the defect based on the depth D1 of the shallow defect and the size X1 of the defect.

The depth determination unit 13 determines that the defect is deep (as a blowhole, for example) in step S106 when the ratio Y is larger than the threshold N, and the process proceeds to step S108. In step S108, the volume calculation unit 14 sets the depth D2 of the defect determined as being deep to a larger value than the depth D1. The volume calculation unit 14 further calculates the volume of the defect based on the depth D2 of the defect and the size X1 of the defect.

In step S109, the volume calculation unit 14 adds up the volumes of the all defects calculated in step S107 and step S108 to calculate the sum of the volumes of the defects. In step S110, the quality determination unit 15 determines whether the sum of the volumes of the defects calculated by the volume calculation unit 14 is the allowable value or smaller. The process proceeds to step S111 when the sum of the volumes of the defects is the allowable value or smaller, and the quality determination unit 15 determines that the inspection object is fine and allowed to be marketed. When the sum of the volumes of the defects calculated by the volume calculation unit 14 is larger than the allowable value in step S110, the process proceeds to step S112, and the quality determination unit 15 determines that the inspection object is inferior.

According to the embodiment of the present invention, the binarization processing is implemented twice with respect to the two-dimensional image by use of different binarization thresholds, so as to detect two sizes X1 and X2 of each defect, calculate the ratio Y of the two sizes X1 and X2 (Y=X2/X1), and determine the depth of each defect depending on the ratio Y. As compared with the conventional case of evaluating defects only based on the size thereof, or setting the depth of defects uniformly to an estimated maximum value, the embodiment of the present invention can determine the depth of each defect with high accuracy and calculate the volume of each defect with high accuracy.

In addition, since the volumes of all defects are added up according to the determination results of the depths of the defects to determine whether the sum of the volumes of the defects is the allowable value or smaller, the quality of the product can be determined with high accuracy.

Further, since the cylinder block 101 of the engine is used as the inspection object, relatively deep blowholes and relatively shallow pits, which are the main surface defects of the cylinder block 101 of the engine, can be discriminated with high accuracy.

Further, since the sum of the volumes of the defects calculated by the volume calculation unit 14 is fed back to the processing such as spraying or aftertreatment, and the processing conditions are changed successively such that the sum of the volumes of the defects is constant or is the allowable value or smaller, the occurrence of defects can be prevented in advance.

First Modified Example

Although the embodiment of the present invention was illustrated by the two sets of binarization processing, a first modified example exemplifies a case in which the binarization processing is implemented three times, and the relative depth of each defect is evaluated in three stages.

Figures 10A, 10B:
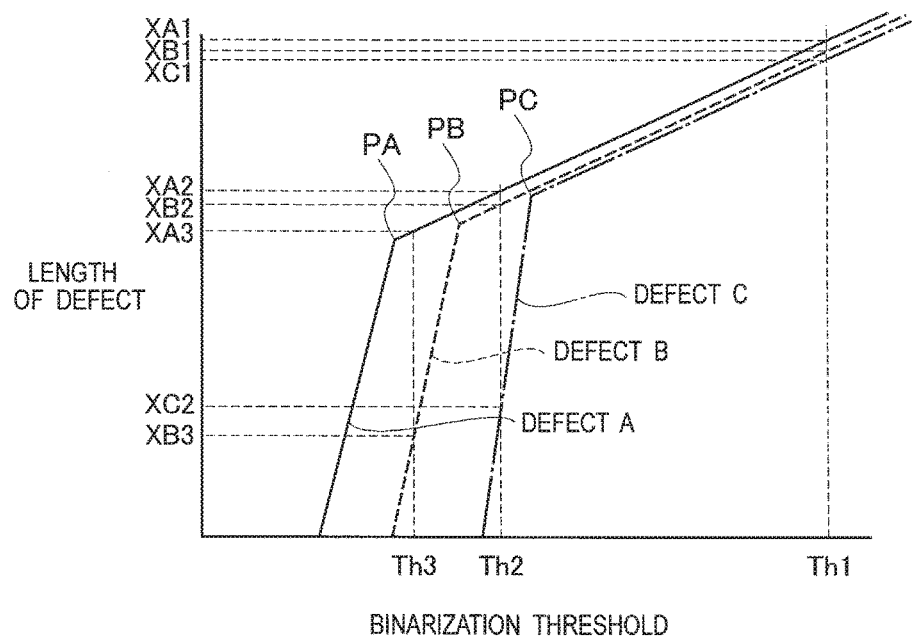
FIG. 10(a) is a graph showing a relationship between a binarization threshold and a defect size according to a first modified example.
FIG. 10(b) is a table showing determination results of a defect depth according to the first modified example.

The binarization processing unit 11 implements (first to third) binarization processing three times by use of different first to third binarization thresholds, so as to calculate first to third sizes with respect to the same defect. FIG. 10(a) exemplifies a case in which there are defects A, B, and C. As shown in FIG. 10(a), the length of the respective defects A to C linearly decreases as the binarization threshold decreases, and a degree of variation of the length sharply increases at the respective inflection points PA, PB, and PC.

The binarization processing unit 11 subjects the respective defects A, B, and C to the binarization processing three times by use of the first to third binarization thresholds Th1 to Th3, so as to calculate the sizes XA1, XA2, and XA3 of the defect A, the sizes XB1, XB2, and XB3 of the defect B, and the sizes XC1 and XC2 of the defect C. The defect C is not detected at the third binarization processing, and the size of the defect C calculated results in 0.

For example, with regard to the defect A, the ratio calculation unit 12 calculates a first ratio Y1 of the second size XA2 to the first size XA1 (Y1=XA2/XA1). The ratio calculation unit 12 also calculates a second ratio Y2 of the third size XA3 to the first size XA1 (Y2=XA3/XA1). The ratio calculation unit 12 repeats the same calculations for the defects B and C to obtain the respective first and second ratios, as in the case of the defect A.

The depth determination unit 13 evaluates the relative depth of the surface defect based on the first and second ratios Y1 and Y2 in three stages. In particular, the depth determination unit 13 compares the first and second ratios Y1 and Y2 each with the threshold N, so as to determine the depth of the defect twice. The thresholds N used in the two determination steps may be the same or different from each other. The depth determination unit 13 comprehensively determines the depth of the defect based on the two determination results.

With regard to the respective defects A, B, and C, the depth determination unit 13 determines whether the first ratio Y1 is the threshold N or smaller in the first determination, and determines whether the second ratio Y2 is the threshold N or smaller in the second determination. As shown in FIG. 10(b), since the two depth determination results for the defect A are both "deep", the defect A is comprehensively determined as being the deepest. Since one of the two depth determination results for the defect B is "deep" and the other is "shallow", the defect B is comprehensively determined as having an intermediate depth. Since the two depth determination results for the defect C are both "shallow", the defect C is comprehensively determined as being the shallowest.

The volume calculation unit 14 sets the depth of each defect in the three stages according to the determination results obtained by the depth determination unit 13. For example, the volume calculation unit 14 sets the depth D1 of the defect A determined as being the deepest to 10 μm, sets the depth D2 of the defect B determined as having an intermediate depth to 50 μm, and sets the depth D3 of the defect C determined as being the shallowest to 100 μm.

The other configurations are substantially the same as those according to the embodiment of the present invention, and the overlapping explanations are not repeated below.

Figure 11:
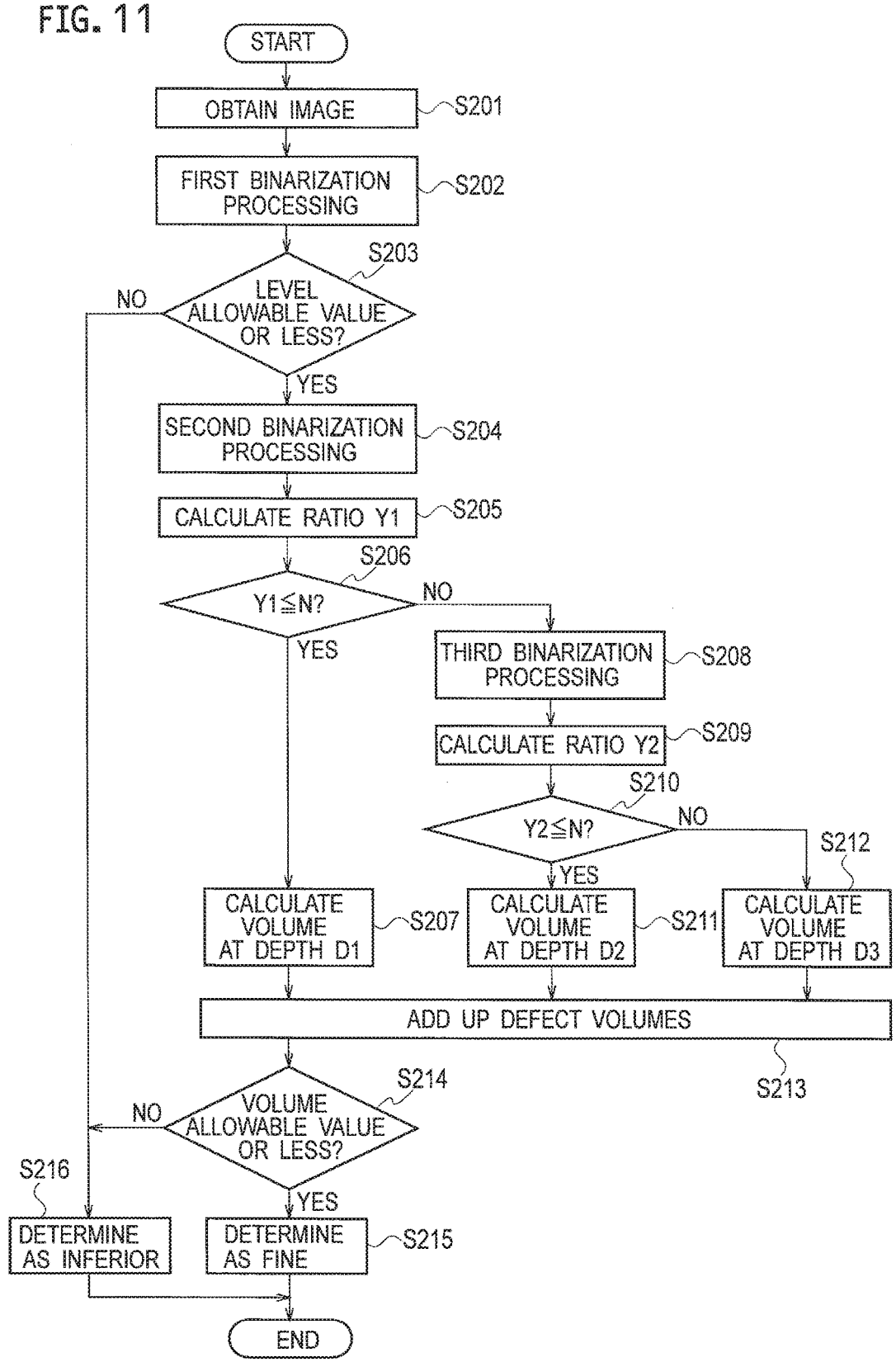
FIG. 11 is a flowchart showing an example of a surface defect detection method according to the first modified example.

Next, an example of a surface defect detection method according to the first modified example is described below with reference to the flowchart shown in FIG. 11.

The process from step S201 to step S205 is the same as the process from step S101 to step S105 shown in FIG. 9, and the overlapping explanations are not repeated below. In step S206, the depth determination unit 13 determines whether the first ratio Y1 is the threshold N or smaller. When the first ratio Y1 is the threshold N or smaller, the depth of the defect is determined as being the shallowest among the three stages, and the process proceeds to step S207, while skipping the third binarization processing. In step S207, the volume calculation unit 14 sets the depth D1 of the defect determined as being the shallowest, and calculates the volume of the defect by use of the depth D1.

When the first ratio Y1 is determined as being larger than the threshold N in step S206, the process proceeds to step S208. In step S208, the binarization processing unit 11 implements the third binarization processing by use of the third binarization threshold Th3, and calculates the size X3 of the defect. In step S209, the ratio calculation unit 12 calculates the second ratio Y2 of the size X3 obtained by the third binarization processing to the size X1 obtained by the first binarization processing (Y2=X3/X1).

In step S210, it is determined whether the second ratio Y2 is the threshold N or smaller. When the second ratio Y2 is the threshold N or smaller, the depth of the defect is determined as being an intermediate level, and the process then proceeds to step S211. In step S211, the volume calculation unit 14 sets the depth D2 (>D1) of the defect determined as being an intermediate level, and calculates the volume of the defect by use of the depth D2. When the second ratio Y2 is larger than the threshold N in step S210, the depth of the defect is determined as being the deepest, and the process then proceeds to step S212. In step S212, the voltage calculation unit 14 sets the depth D3 (>D2) of the defect determined as being the deepest, and calculates the volume of the defect by use of the depth D3.

In step S213, the sum of the volumes of the all defects obtained in step S207, step S211, and step S212 is calculated. The process from step S214 to step 216 is the same as the process from step S110 to step S112 shown in FIG. 9, and the overlapping explanations are not repeated below.

According to the first modified example, the binarization processing is implemented three times by use of the three different binarization thresholds to evaluate the depth of each defect in three stages, so as to calculate the volume of each defect with higher accuracy. Although the first modified example was illustrated by the three sets of the binarization processing, the first modified example may implement the binarization processing four times or more by use of four different binarization thresholds or more, so as to evaluate the depth of each defect in four stages or more.

Second Modified Example

A second modified example exemplifies a case in which the depth of each defect is determined in several stages, while the binarization processing is implemented twice.

Figures 12, 12A, 12B:
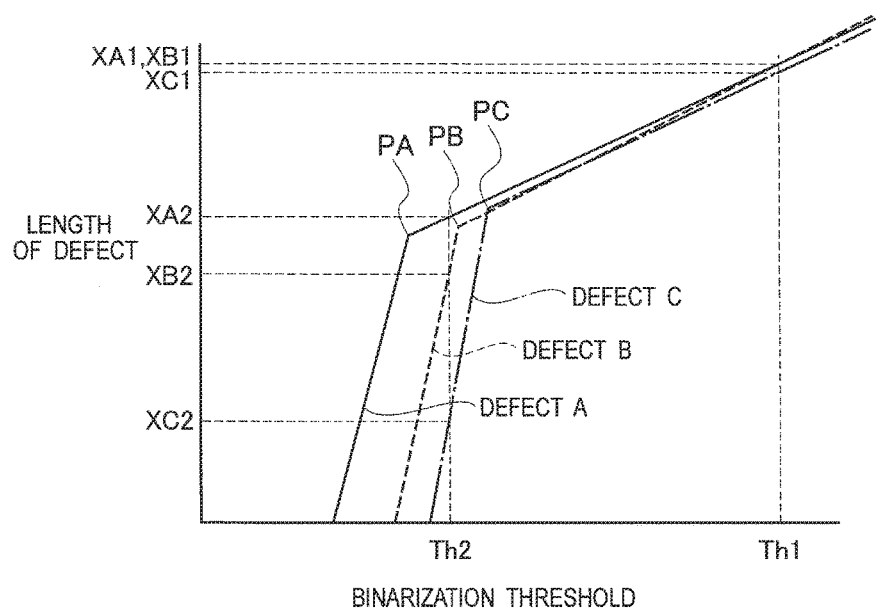
FIG. 12(a) is a graph showing a relationship between a binarization threshold and a defect size according to a second modified example.
FIG. 12(b) is a table showing determination results of a defect depth according to the second modified example.

As shown in FIG. 12(a), the defects A, B, and C are each subjected to the binarization processing twice by use of the two binarization thresholds Th1 and Th2, so as to calculate the sizes XA1 and XA2 of the defect A, the sizes XB1 and XB2 of the defect B, and the sizes XC1 and XC2 of the defect C. With regard to the defect A, the ratio calculation unit 12 calculates the ratio Y of the second size XA2 to the first size XA1 (Y=XA2/XA1). The ratio calculation unit 12 repeats the same calculation for the defects B and C to obtain the respective ratios, as in the case of the defect A.

The depth determination unit 13 compares the ratio Y calculated by the ratio calculation unit 12 with each of multiple (two) different thresholds N1 and N2, so as to determine the depth of each defect several times (twice). The thresholds N1 and N2 may be determined as appropriate depending on the product or the type of defects. The threshold N1 is set to 0.5, for example. The threshold N2 is set to 0.7, for example, which is larger than the threshold N1.

With regard to the respective defects A, B, and C, the depth determination unit 13 determines whether the ratio Y is the threshold N1 or smaller in the first determination, and determines whether the ratio Y is the threshold N2 or smaller in the second determination. The depth determination unit 13 comprehensively determines the depth of each defect according to the two determination results.

As shown in FIG. 12(b), with regard to the defect A, since the ratio Y is the threshold N1 or smaller in the first determination, and the ratio Y is the threshold N2 or smaller in the second determination, the defect A is comprehensively determined as being the deepest. With regard to the defect B, since the ratio Y is larger than the threshold N1 in the first determination, and the ratio Y is the threshold N2 or smaller in the second determination, the defect B is comprehensively determined as having an intermediate depth. With regard to the defect C, since the ratio Y is larger than the threshold N1 in the first determination, and the ratio Y is larger than the threshold N2 also in the second determination, the defect C is comprehensively determined as being the shallowest.

The volume calculation unit 14 sets the depth of each defect in the three stages according to the determination results obtained by the depth determination unit 13. For example, the volume calculation unit 14 sets the depth D1 of the defect A determined as being the deepest to 10 μm, sets the depth D2 of the defect B determined as having an intermediate depth to 50 μm, and sets the depth D3 of the defect C determined as being the shallowest to 100 μm.

The other configurations are substantially the same as those according to the embodiment of the present invention, and the overlapping explanations are not repeated below.

Figure 13:
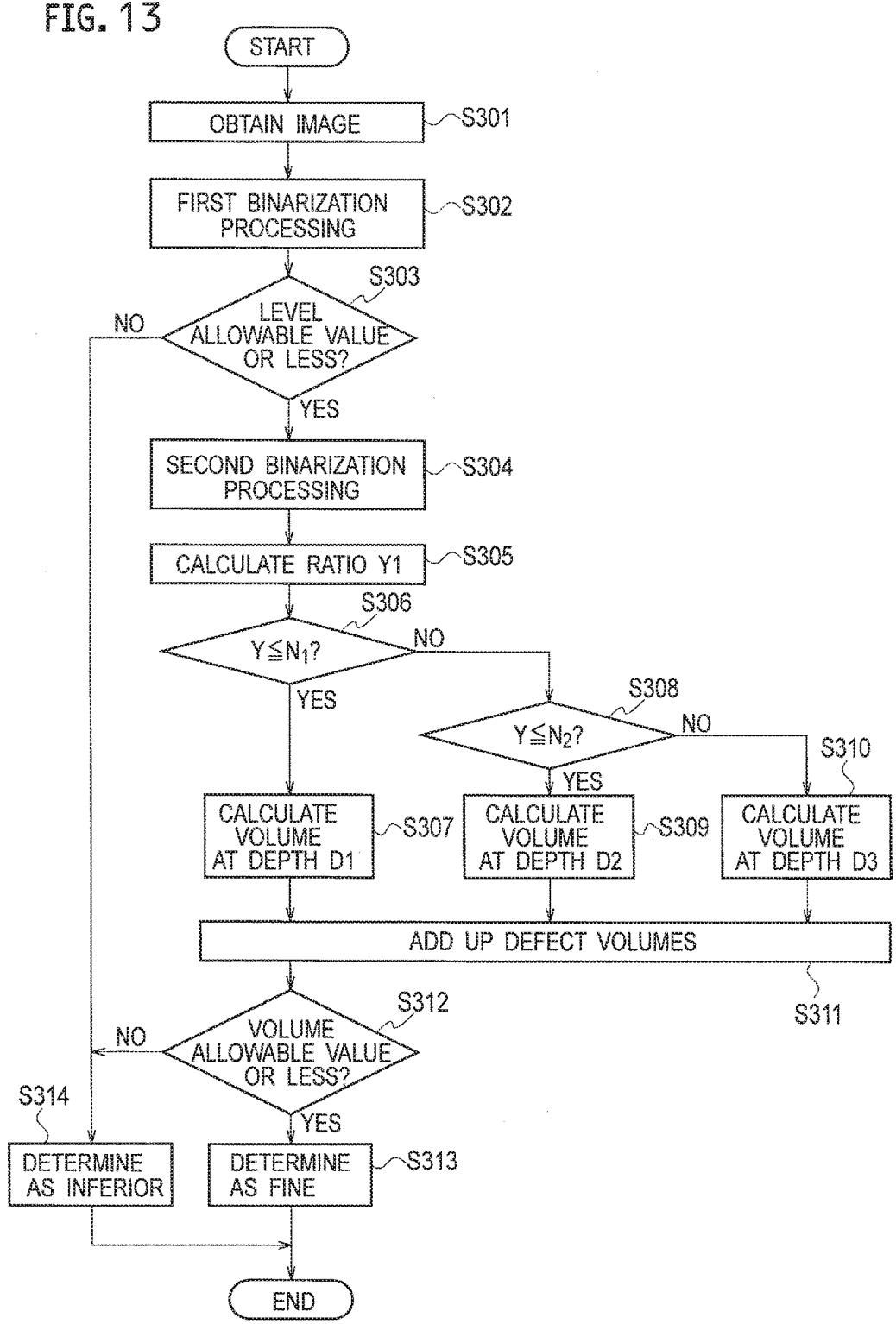
FIG. 13 is a flowchart showing an example of a surface defect detection method according to the second modified example.

Next, an example of a surface defect detection method according to the second modified example is described below with reference to the flowchart shown in FIG. 13.

The process from step S301 to step S305 is the same as the process from step S101 to step S105 shown in FIG. 9, and the overlapping explanations are not repeated below. In step S306, the depth determination unit 13 determines whether the ratio Y is the threshold N1 or smaller. When the ratio Y is the threshold N1 or smaller, the depth of the defect is determined as being the shallowest, and the process then proceeds to step S307. In step S307, the volume calculation unit 14 sets the depth D1 of the defect determined as being the shallowest, and calculates the volume of the defect by use of the depth D1.

When the ratio Y is determined as being larger than the threshold N1 in step S306, the process proceeds to step S308. In step S308, the depth determination unit 13 determines whether the ratio Y is the threshold N2 or smaller, which is larger than the threshold N1. When the ratio Y is the threshold N2 or smaller, the depth of the defect is determined as being an intermediate level, and the process then proceeds to step S309. In step S309, the volume calculation unit 14 sets the depth D2 (>D1) of the defect determined as being an intermediate level, and calculates the volume of the defect by use of the depth D2.

When the ratio Y is larger than the threshold N2 in step S308, the depth of the defect is determined as being the deepest, and the process then proceeds to step S310. In step S310, the voltage calculation unit 14 sets the depth D3 (>D2) of the defect determined as being the deepest, and calculates the volume of the defect by use of the depth D3.

In step S311, the sum of the volumes of the all defects obtained in step S307, step S309, and step S310 is calculated. The process from step S312 to step 314 is the same as the process from step S110 to step S112 shown in FIG. 9, and the overlapping explanations are not repeated below.

According to the second modified example, each defect is subjected to the depth determination twice by use of the different thresholds N1 and N2 to evaluate the depth of the defect in three stages, so as to obtain the depth and volume of the defect with higher accuracy. Although the second modified example was illustrated by the case in which each defect is subjected to the depth determination twice by use of the two thresholds N1 and N2 to comprehensively evaluate the depth of the defect in three stages, the second modified example is not limited thereto. Alternatively, the depth determination unit 13 may subject the defect to the depth determination three times or more in two stages by use of three different binarization thresholds or more, so as to comprehensively evaluate the depth of each in four stages or more.

Other Embodiments

While the embodiment of the present invention has been described above, it should be understood that the present invention is not intended to be limited to the descriptions and the drawings composing part of this disclosure. Various alternative embodiments, examples, and technical applications will be apparent to those skilled in the art according to this disclosure.

For example, the embodiment of the present invention has exemplified the internal surface of the cylinder bore 102 of the cylinder block 101 of the engine, as an example of the inspection object by the defect detection device 1, but is not limited thereto. The defect detection device 1 is applicable to various types of products which may have surface defects. Defects are not limited to any particular type, and the size of defects detected by use of binarization thresholds may vary linearly.

REFERENCE SIGNS LIST

1 DEFECT DETECTION DEVICE
2 CONTROL DEVICE
3 IMAGING DEVICE
4 PROCESSING DEVICE
11 BINARIZATION PROCESSING UNIT
12 RATIO CALCULATION UNIT
13 DEPTH DETERMINATION UNIT
14 VOLUME CALCULATION UNIT
15 QUALITY DETERMINATION UNIT
30 DRIVE UNIT
31 LIGHT SOURCE
32 MIRROR
33 IMAGING UNIT
41 GUN BODY
42 SPRAY GUN
101 CYLINDER BLOCK
102 CYLINDER BORE

What is claimed is:

1. A defect detection device comprising:
   a camera configured to image an image of an inspection object;
   a binarization processor configured to subject the image to first and second binarization processing by use of a first binarization threshold and a second binarization threshold different from the first binarization threshold, so as to calculate first and second sizes for an identical defect in the image;
   a ratio calculation processor configured to calculate a first ratio of the second size to the first size; and
   a depth determination processor configured to determine a depth of the defect depending on the first ratio,
   wherein the first binarization threshold is larger than the second binarization threshold, and
   a size of the identical defect includes at least one of a defect area and a defect length.

2. The defect detection device according to claim 1, further comprising:
   a volume calculation processor configured to calculate a volume of the defect depending on the depth of the defect determined, and calculate a sum of volumes of all defects in the image; and
   a quality determination processor configured to determine whether the inspection object is fine or inferior according to the sum of the volumes of the all defects.

3. The defect detection device according to claim 1, wherein:
   the binarization processing processor subjects the image to third binarization processing by use of a third binarization threshold different from the first binarization threshold and the second binarization threshold, so as to calculate a third size for the identical defect in the image;
   the ratio calculation processor calculates a second ratio of the third size to the first size; and
   the depth determination processor determines a depth of the defect depending on the first and second ratios.

4. The defect detection device according to claim 1, wherein the depth determination processor compares the first ratio with each of a plurality of thresholds different from each other to determine depths of the defect several times, so as to comprehensively evaluate the depth of the defect according to the depths determined several times.

5. The defect detection device according to claim 1, wherein:
   the inspection object is a cylinder block of an engine; and
   the defect includes at least a pit and a blowhole.

6. A production system comprising:
   a defect detection device comprising:
      a camera configured to image an image of an inspection object;
      a binarization processor configured to subject the image to first and second binarization processing by use of a first binarization threshold and a second binarization threshold different from the first binarization threshold, so as to calculate first and second sizes for an identical defect in the image;

a ratio calculation processor configured to calculate a first ratio of the second size to the first size;

a depth determination processor configured to determine a depth of the defect depending on the first ratio; and a volume calculation processor configured to calculate a volume of the defect depending on the depth of the defect determined, and calculate a sum of volumes of all defects in the image, and a gun body and a spray gun attached to the gun body configured to arrange a processing condition for the inspection object according to the sum of the volumes of the all defects, wherein the first binarization threshold is larger than the second binarization threshold, and a size of the identical defect includes at least one of a defect area and a defect length.

* * * * *